United States Patent
Pimenta et al.

(10) Patent No.: US 11,458,081 B2
(45) Date of Patent: Oct. 4, 2022

(54) PERSONAL CARE COMPOSITIONS

(71) Applicant: Colgate-Palmolive Company, New York, NY (US)

(72) Inventors: Paloma Pimenta, Staten Island, NY (US); Farrah Syed, Hamilton, NJ (US); Jesse Reed, Flemington, NJ (US)

(73) Assignee: Colgate-Palmolive Company, New York, NY (US)

( * ) Notice: Subject to any disclaimer, the term of this patent is extended or adjusted under 35 U.S.C. 154(b) by 179 days.

(21) Appl. No.: 16/488,338

(22) PCT Filed: Feb. 27, 2018

(86) PCT No.: PCT/US2018/019813
§ 371 (c)(1),
(2) Date: Aug. 23, 2019

(87) PCT Pub. No.: WO2018/160509
PCT Pub. Date: Sep. 7, 2018

(65) Prior Publication Data
US 2021/0205190 A1 Jul. 8, 2021

(30) Foreign Application Priority Data

Feb. 28, 2017 (EP) .................... 17158294

(51) Int. Cl.
*A61K 8/34* (2006.01)
*A61K 8/06* (2006.01)
*A61Q 19/00* (2006.01)
*A61K 8/37* (2006.01)

(52) U.S. Cl.
CPC .......... *A61K 8/345* (2013.01); *A61K 8/062* (2013.01); *A61Q 19/00* (2013.01); *A61K 8/37* (2013.01); *A61K 2800/524* (2013.01)

(58) Field of Classification Search
CPC .......... A61K 8/39; A61K 8/345; A61K 8/368
See application file for complete search history.

(56) References Cited

U.S. PATENT DOCUMENTS

| | | | |
|---|---|---|---|
| 5,683,683 A | 11/1997 | Scafidi | |
| 6,121,214 A * | 9/2000 | Exner | A61K 8/39 510/130 |
| 9,492,364 B2 | 11/2016 | Rudolph et al. | |
| 9,700,494 B2 | 7/2017 | Potechin et al. | |
| 2005/0112081 A1* | 5/2005 | Loeffler | A61K 8/86 424/70.31 |
| 2007/0190005 A1* | 8/2007 | Rozsa | A61K 8/368 424/70.1 |
| 2011/0300091 A1 | 12/2011 | Demson et al. | |
| 2012/0172433 A1* | 7/2012 | Yamamoto | A61K 8/31 514/552 |
| 2012/0231059 A1* | 9/2012 | Schmitz | A61K 8/345 510/141 |
| 2013/0183358 A1* | 7/2013 | Fernandez Botello | C11D 3/362 424/401 |
| 2014/0004163 A1* | 1/2014 | Mundschau | A61K 8/0208 424/401 |
| 2015/0252302 A1* | 9/2015 | Rieth | A61Q 5/10 8/405 |
| 2017/0042798 A1 | 2/2017 | Wenzel et al. | |

FOREIGN PATENT DOCUMENTS

| | | | |
|---|---|---|---|
| CN | 104352389 | 2/2015 | |
| CN | 105147528 | 12/2015 | |
| EP | 1206933 | 5/2002 | |
| RU | 2434981 | 11/2011 | |
| WO | WO-2007006402 A1 * | 1/2007 | ............... A61Q 5/02 |
| WO | 2011/101153 | 8/2011 | |
| WO | 2015/167545 | 11/2015 | |

OTHER PUBLICATIONS

WO-2007006402-A1 (Espacenet English translation, downloaded Apr. 2021) (Year: 2021).*
International Search Report and Written Opinion of the International Searching Authority in International Application No. PCT/US2018/019813, dated May 14, 2018.

* cited by examiner

*Primary Examiner* — Mark V Stevens

(57) ABSTRACT

Described herein are low pH, high water, personal care compositions providing an acceptable level of micropreservation. Methods of making and using these compositions are also described.

13 Claims, No Drawings

PERSONAL CARE COMPOSITIONS

BACKGROUND

Maintaining adequate preservation in high water systems is generally a challenge for product developers. And, maintaining adequate preservation in high water systems using soft preservation systems at low pH has proven to be particularly challenging. As such, there remains a need for low pH, high water personal care compositions which are stable and demonstrate an adequate level of micropreservation.

Embodiments of the present invention are designed to meet these, and other, needs.

BRIEF SUMMARY

In some embodiments, the present invention provides an aqueous personal care composition comprising: greater than about 60 wt. % water; a preservative system; and a preservative booster comprising a mixture of pegylated alkyl glycerides.

Other embodiments provide a high-water personal care composition comprising: greater than about 60 wt. % water; and an effective amount of an antimicrobial system consisting essentially of: a $C_3$-$C_{10}$ alkyl polyol; sodium benzoate; and a mixture of pegylated alkyl glycerides.

Further embodiments provide methods of using the compositions described herein to moisturize and/or improve the tonicity of the skin.

DETAILED DESCRIPTION

As used herein, the term "oil-in-water emulsion" means a composition consisting of an aqueous dispersing continuous phase and an oily dispersed discontinuous phase.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or any variation of these terms, when used in the claims and/or the specification includes any measurable decrease or complete inhibition to achieve a desired result.

The terms "effective" or "effective amount" as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

The compositions and methods described herein can "comprise," "consist essentially of," or "consist of" any of the ingredients disclosed throughout the specification. When the transitional phrase "consist(s) essentially of" is used in a claim, the basic and novel characteristic of the claimed composition is its ability to remain stable, maintain an acceptable level of antimicrobial resistance, moisturize skin, while also having a cosmetically acceptable feel.

Some embodiments of the present invention provide an aqueous personal care composition comprising: greater than about 60 wt. % water; a preservative system; and a preservative booster comprising a mixture of pegylated alkyl glycerides.

In some embodiments, the compositions described herein comprise greater than about 50 wt. % water. In some embodiments, the compositions described herein comprise greater than about 55 wt. % water. In some embodiments, the compositions described herein comprise greater than about 60 wt. % water. In some embodiments, the compositions described herein comprise greater than about 65 wt. % water. In some embodiments, the compositions described herein comprise greater than about 70 wt. % water. In some embodiments, the compositions described herein comprise greater than about 75 wt. % water. In some embodiments, the compositions described herein comprise about 75 wt. % water. In some embodiments, the compositions described herein comprise about 77 wt. % water.

In some embodiments, the aqueous personal care composition comprises a hydrophobic component comprising: a wax, a silicone, an oil extract; or a combination of two or more thereof.

Other embodiments provide aqueous personal care compositions wherein the composition is an oil-in-water emulsion.

In some embodiments, the compositions of the present invention comprise a pH modifying agent to adjust the pH of the composition. Suitable pH modifying agents, which may be used alone or in combination, include any of the following: mineral acids such as hydrochloric acid, phosphoric acid and sulfuric acid, organic acids such as benzoic acid, citric acid, lactic acid, maleic acid, malic acid, tartaric acid, adipic acid, gluconic acid and salts thereof.

In some embodiments, the pH modifying agent comprises lactic acid, sodium lactate or a combination thereof. The amount of pH modifying agent used in the composition is dictated by the desired pH of the final product, but is typically from about 0.1 wt. % to about 5.0 wt % of the total composition, e.g. about 4 wt. % of the total composition. In the context of the present invention, the pH described and claimed herein is that of the neat product taken at 25° C.

In some embodiments, the aqueous personal care composition has a pH of from about 3.0 to about 5.0. In further embodiments, the aqueous personal care composition has a pH of from about 3.5 to about 4.9. In certain embodiments, the aqueous personal care composition has a pH of from about 4.0 to about 4.6. Still further embodiments provide aqueous personal care compositions having a pH of 4.0, 4.1, 4.2, 4.3, 4.4, 4.5, or 4.6. In some embodiments, the compositions of the present invention are formulated to a pH that presents minimal disruption to the skin.

Further embodiments provide compositions having a viscosity greater than about 5000 centipoise (cps). Some embodiments provide compositions having a viscosity greater than about 5500 cps. Still further embodiments provide compositions having a viscosity greater than about 6000 cps. Yet other embodiments provide compositions having a viscosity greater than about 6500 cps. Certain embodiments provide compositions having a viscosity greater than about 7000 cps. While other embodiments provide compositions having a viscosity greater than about 7500 cps. Some embodiments provide compositions having a viscosity greater than about 10000, 15000, 20000, 25000, 30000, 35000, 40000, 45000 or 50000 cps.

In the context of the present invention, viscosity is measured by Brookfield Helipath Spindle 92, at 10 RPM and 25° C.

In some embodiments, the compositions of the present invention provide a micro robustness index (MRI) of greater than 0.75. In other embodiments, the compositions of the present invention provide a MRI of greater than 0.80. In certain embodiments, the compositions of the present invention provide a MRI of greater than 0.85. While in other embodiments, the compositions of the present invention provide a MRI of greater than 0.90. Yet other embodiments provide compositions having a MRI of greater than 0.95. Still further embodiments provide compositions having a MRI of greater than 1.00. In some embodiments, the compositions of the present invention provide a MRI of greater than 1.05. In other embodiments, the compositions of the present invention provide a MRI of greater than 1.10. In further embodiments, the compositions of the present invention provide a MRI of 1.13 or 1.16.

In some embodiments, the compositions of the present invention include a preservative system comprising less than about 1 wt. % of the total composition. In some embodiments, the compositions of the present invention include a preservative system comprising less than about 0.95 wt. % of the total composition. In some embodiments, the compositions of the present invention include a preservative system comprising less than about 0.90 wt. % of the total composition. In some embodiments, the compositions of the present invention include a preservative system comprising less than about 0.85 wt. % of the total composition. In some embodiments, the compositions of the present invention include a preservative system comprising less than about 0.80 wt. % of the total composition.

In some embodiments, the present invention provides compositions wherein the ratio of preservative system to preservative booster is from about 3 to 1 to about 6 to 1. In some embodiments, ratio of preservative system to preservative booster is about 4 to 1.

In some embodiments, the preservative system comprises a $C_3$-$C_{10}$ alkyl polyol, and sodium benzoate. In some embodiments, the $C_3$-$C_{10}$ alkyl polyol is caprylyl glycol.

In some embodiments, the preservative booster comprises PEG-9 cocoglycerides. In some embodiments, the preservative booster comprises PEG-6 caprylic/capric glyceride. In other embodiments, the preservative booster comprises a mixture of PEG-9 cocoglycerides and PEG-6 caprylic/capric glyceride.

In some embodiments, the compositions of the present invention comprise a source of ricinoleic acid. In some embodiments, the source of ricinoleic acid is castor oil.

Other embodiments provide a high-water personal care composition comprising: greater than about 60 wt. % water; and an effective amount of an antimicrobial system consisting essentially of: a $C_3$-$C_{10}$ alkyl polyol; sodium benzoate; and a mixture of pegylated alkyl glycerides.

In some embodiments, the compositions of the present invention comprise greater than about 1 wt. % of a pH modifying agent; greater than about 0.5 wt. % of sodium benzoate; greater than about 0.3 wt. % of a $C_3$-$C_{10}$ alkyl polyol; and greater than about 0.1 wt. % of a pegylated alkyl glyceride. Other embodiments provide In some embodiments, the present invention provides a method of improving the skin tone of a mammal, comprising applying any one of the compositions described herein to the skin of a mammal in need thereof. Other embodiments provide methods of moisturizing the skin of a mammal, comprising applying any one of the compositions described herein to the skin of a mammal in need thereof.

In some embodiments, compositions of the present invention include an emulsifying agent. In some embodiments, the emulsifying agent includes, but is not limited to, ethoxylated carboxylic acids, ethoxylated glycerides, glycol esters and derivatives thereof, monoglycerides, polyglyceryl esters, polyhydric alcohol esters and esters, sorbitan/sorbitol esters, triesters of phosphoric acid, ethoxylated-fatty alcohols, propoxylated polyoxyethylene (POE) esters and the like and mixtures thereof. Particularly preferred are glyceryl stearate, PEG-100 stearate, sorbitan stearate, PEG-40 stearate, steareth-2, steareth-20, steareth-100, polysorbate-20, laureth-12, laureth-23, polysorbate 80, sucrose distearate, glyceryl oleate, and the like as well as mixtures thereof.

In some embodiments, at least about 1 wt. % of the composition comprises an emulsifying agent. In other embodiments, from about 1 wt. % to about 10 wt. % of the composition comprises an emulsifying agent.

The compositions of the present invention must be protected against the growth of potentially harmful microorganisms, and therefore preservatives are added as a routine. Generally from one tenth of one percent by weight to one percent by weight of preservatives are adequate, with 0.8 weight percent preferred by the present compositions. Suitable preservatives include, but are not limited to, alkyl esters of para-hydroxybenzoic acid, hydantoin derivatives, propionate salts, quaternium-15, imidazolidinyl urea, EDTA and its salts, and the like (e.g. methyl and propyl para-hydroxybenzoates and 2-phenoxyethanol). The preservatives should be selected having regard for the use of the composition and possible incompatibilities between the preservatives and the other ingredients.

Some embodiments of the present invention comprise rheology modifying agents or thickeners. In some embodiments, the rheology modifier comprises a polysaccharaide. In some embodiments, the polysaccharide may be chosen from fructans, gellans, glucans, amylose, amylopectin, glycogen, pullulan, dextrans, celluloses and derivatives thereof, in particular methylcelluloses, hydroxyalkylcelluloses, ethylhydroxyethylcelluloses and carboxymethylcelluloses, mannans, xylans, lignins, arabans, galactans, galacturonans, alginate-based compounds, chitin, chitosans, glucuronoxylans, arabinoxylans, xyloglucans, glucomannans, pectic acids and pectins, arabinogalactans, carrageenans, agars, glycosaminoglycans, gum arabics, tragacanth gums, ghatti gums, karaya gums, locust bean gums, galactomannans such as guar gums and nonionic derivatives thereof, in particular hydroxypropyl guar, and ionic derivatives thereof, biopolysaccharide gums of microbial origin, in particular scleroglucan or xanthan gums, mucopolysaccharides, and in particular chondroitin sulfates, and mixtures thereof.

In some embodiments, compositions of the present invention comprise at least one emollient. As used herein, the term "emollient" means a material that protects against wetness or irritation, softens, soothes, supples, coats, lubricates, moisturizes, protects and/or cleanses the skin; the term "protectant" means a material which protects injured or exposed skin or mucous membrane surface from harmful or annoying stimuli. In some embodiments, the emollient will have either a plastic or liquid consistency at room temperatures.

Suitable emollients can include those hydrocarbons, or mixtures of hydrocarbons, having chain lengths of from 16 to 50 carbon atoms. Hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Other suitable emollients include natural fats and natural oils. In certain embodiments the emollient can be selected from the group consisting of petrolatum, mineral oil and mixtures thereof. In certain embodiments the emollient can be derived from a renewable resource.

Other suitable emollients can include fatty acid ester type emollients, alkyl ethoxylate type emollients, fatty alcohol type emollients, and combinations thereof.

Suitable emollients may also include natural oils or fats, or natural oil or fat derivatives, in particular of plant or animal origin. Non-limiting examples include oleic canola Oil (*Brassica eampestris, B. napus, B. rapa*; characterized by having an oleic content greater than 70%, e.g., hi oleic canola oil, very high oleic canola oil, or partially hydrogenated canola oil), marula kernel oil (*Sclerocarya birrea*), palm oil (*Elaeis guineensis* Oil), palm olein, palm stearin, palm superolein, pecan oil, pumpkin seed oil, oleic safflower oil (*Carthamus tinetorius*; characterized by having an oleic content of greater than about 30% and omega-6 fatty acid content of less than about 50%, e.g., hi oleic safflower oil), sesame oil (*Sesamum indicum, S. oreintale*), soybean oil (*Glycine max*, e.g., hi oleic soybean, low linolenic soybean oil, partially hydrogenated), oleic sunflower oil (*Helianthus annus*; characterized by having an oleic content of greater than about 40%, e.g., mid oleic sunflower or high oleic sunflower oil), apricot oil, babassu oil, castor oil, coconut oil, cod liver oil, hydrogenated corn oil, hydrogenated cottonseed oil, hazelnut oil, jojoba oil, macadamia oil, meadowfoam seed oil, mink oil, maringa oil, marula oil, mortierella oil, palm kernel oil, hydrogenated peanut oil, hydrogenated rapeseed oil, rose hip oil, hydrogenated safflower oil, hydrogenated soybean oil, hydrogenated sunflower oil, hydrogenated walnut oil, hydrogenated wheat germ oil, or the hardened derivatives thereof.

Other non-limiting examples of fats and oils suitable skin care active options herein include: butter, C12-C18 acid triglyceride, caprylic/capric/lauric triglyceride, caprylic/capric/linoleic triglyceride, caprylic/capric/stearic triglyceride, caprylic/capric triglyceride, cocoa butter, C10-C18 triglycerides, egg oil, epoxidized soybean oil, glyceryl triacetyl hydroxystearate, glyceryl triacetyl ricinoleate, glycosphingolipids, hydrogenated castor oil, hydrogenated castor oil laurate, hydrogenated coconut oil, hydrogenated C12-C18 triglycerides, hydrogenated fish oil, hydrogenated lard, hydrogenated menhaden oil, hydrogenated mink oil, hydrogenated orange roughy oil, hydrogenated shark liver oil, hydrogenated tallow, hydrogenated vegetable oil, lanolin and lanolin derivatives, lanolin alcohol, lard, lauric/palmitic/oleic triglyceride, lesquerella oil, maleated soybean oil, neatsfoot oil, oleic/linoleic triglyceride, oleic/palmitic/lauric/myristic/linoleic triglyceride, oleostearine, olive husk oil, omental lipids, pengawar djambi oil, pentadesma butter, phospholipids, shea butter, tallow, tribehenin, tricaprin, tricaprylin, triheptanoin, trihydroxymethoxystearin, trihydroxystearin, triisononanoin, triisostearin, trilaurin, trilinolein, trilinolenin, trimyristin, trioctanoin, triolein, tripalmitin, trisebacin, tristearin, triundecanoin, and the like, as well as mixtures thereof.

Oleic canola oil, palm oil, sesame oil, hi oleic safflower oil, hi oleic soybean oil, mid oleic sunflower oil, and high oleic sunflower oil are common plant-bred derived oils and may be also be derived from non-genetically modified organisms (non-GMO).

In certain embodiments, the emollient can further comprise a blend of oils, including those described supra, as well as additional oil materials. Suitable additional emollients can include acai berry oil, almond oil, avocado oil, beech oil, brazil nut oil, *Camelina sativa* oil (family Brassicaceae, e.g. *Camelina sativa*, Gold of Pleasure, False Flax, etc.), camellia seed oil, canola oil, carrot seed oil, cashew nut oil, castor oil, cherry kernel oil, chia oil, corn oil, cottonseed oil, hydrogenated cottonseed oil, evening primrose oil, filbert (hazelnut) oil, grapeseed oil, hemp oil, hickory nut oil, jojoba oil, kukui oil, lanolin, olive oil (*Olea europaea*), macadamia oil, maringa oil, meadowfoam oil, neem oil, palm kernel oil, olive oil, passionflower oil (family *Passiflora, Passiflora incarnata*), peanut oil, peach kernel oil, pistachio nut oil, rapeseed oil, rice bran oil, rose hip oil, safflower oil, sorghum oil, soybean oil, sunflower seed oil, tall oil, vegetable oil, vegetable squalene, walnut oil, wheat germ oil, and mixtures thereof. The oil material of the present invention can be selected from the group consisting of *Camelina sativa* seed oil, oleic canola oil, evening primrose oil, marula kernel oil, palm oil, palm olein, palm stearin, palm superolein, *Passiflora incarnata* seed oil, pecan oil, pumpkin seed oil, oleic safflower oil, sesame oil, soybean oil, oleic sunflower oil, vegetable oil and mixtures thereof.

Yet further embodiments, suitable emollients include silicone oils. In such embodiments the silicone oil may be chosen from non-volatile polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates. In some embodiments the emollient comprises dimethicone.

In some embodiments, to further enhance the stability of the composition, certain antioxidants can be added directly to the mixture of emollients or to the composition as a whole. In some embodiments, the composition comprises from about 0.005% to about 1%, from about 0.01% to about 0.5%, or from about 0.02% to about 0.2%, by weight of the composition, of an antioxidant. In other embodiments, the composition comprises from about 0.0005% to about 1%, from about 0.001% to about 0.75%, or from about 0.002% to about 0.5%, or about 0.3% by weight of the composition, of an antioxidant. Non-limiting examples of suitable antioxidants include a-tocopherol, tocopheryl acetate, β-tocopherol, γ-tocopherol, δ-tocopherol, tocotrienol, rosemary, sesamol, sesamolin, sesamin, catechin, and mixtures thereof.

In some embodiments, the present invention provides high-water personal care compositions comprising: greater than about 60 wt. % water; and an emulsion stabilizing system comprising a fatty alcohol; and a fatty acid ester; wherein the composition has a MRI of greater than 0.75. In some embodiments, the present invention provides high-water personal care compositions comprising: greater than about 60 wt. % water; and an emulsion stabilizing system comprising a fatty alcohol; and a fatty acid ester; wherein the composition has a MRI of greater than 1.00. Some embodiments further comprise a hydrophobic component comprising: a wax, a silicone, an oil extract; or a combination of two or more thereof. In some embodiments, the wax is petrolatum. In certain embodiments, the petrolatum is present in an amount greater than the fatty alcohol.

As used herein, the term "high-water" may refer to compositions comprising greater than about 50 wt. % water, optionally greater than about 55 wt. %, about 60 wt. %, about 65 wt. %, about 70 wt. %, about 75 wt. %, about 80 wt. %, about 85 wt. %, about 90 wt. % or about 95 wt. % water.

In certain embodiments, the compositions are formulated into topical skin care compositions. The compositions can be cosmetic compositions. In other aspects, the compositions can be included in a cosmetic vehicle. Non-limiting examples of cosmetic vehicles are disclosed in other sections of this specification and are known to those of skill in the art. Examples of cosmetic vehicles include creams, lotions, and ointments. In other non-limiting embodiments, the compositions of the present invention can be included in skin moisturizing products such as hand, face, or total body moisturizers. The compositions can also be formulated for topical skin application at least 1, 2, 3, 4, 5, 6, 7, or more times a day during use.

Also described herein are methods of treating or preventing a skin condition comprising topical application of any one of the compositions described in this specification to skin in need thereof, wherein the topical application of the composition treats the skin condition. In one aspect, the method includes moisturizing skin or treating or preventing the appearing of dry skin, flaky skin, or chapped skin. In other aspects, it is contemplated that the compositions can be used to treat or prevent various skin conditions ranging from pruritus, fine lines or wrinkles, sun damaged skin, dermatitis, eczema, and other inflammatory skin conditions. The skin can be facial skin or non-facial skin (e.g., arms, legs, hands, chest, back, feet, etc.).

In some embodiments, the methods described herein further comprise the step of identifying a person in need of treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein.

Exemplary embodiments of the present disclosure will be illustrated by reference to the following examples, which are included to exemplify, but not to limit the scope of the present invention.

EXAMPLES

Example 1

Table 1 (below) describes the formulations for three (3) exemplary compositions of the present invention (Ex. I to Ex. III); and three comparative examples (Comp. Ex. I to Comp. Ex. III).

TABLE 1

| Ingredient | Ex. I | Ex. II | Ex. III | Comp. Ex. I | Comp. Ex. II | Comp. Ex. III |
|---|---|---|---|---|---|---|
| | | | Wt. % | | | |
| Sodium Lactate | 3.10 | 3.10 | 3.10 | 3.10 | 3.10 | 3.10 |
| Lactic Acid | 1.00 | 1.00 | 1.00 | 1.00 | 1.00 | 1.00 |
| Sodium Benzoate | 0.50 | 0.50 | 0.50 | 0.40 | 0.50 | 0.40 |
| Caprylyl Glycol | 0.30 | 0.30 | 0.01 | 0.01 | 0.30 | 0.01 |
| Glyceryl Oleate | 0.50 | 0.50 | 0.50 | 0.50 | 0.50 | 0.50 |
| Petrolatum | 8.00 | 8.00 | 5.00 | 8.00 | 8.00 | 8.00 |
| Cetearyl Alcohol | 2.99 | 2.99 | 6.00 | 2.00 | 2.99 | 2.00 |
| Glyceryl Stearate | 1.25 | 1.25 | 1.25 | 1.00 | 1.25 | 1.00 |

TABLE 1-continued

| Ingredient | Ex. I | Ex. II | Ex. III | Comp. Ex. I | Comp. Ex. II | Comp. Ex. III |
|---|---|---|---|---|---|---|
| | | | Wt. % | | | |
| PEG-100 Stearate | 1.50 | 1.50 | 1.50 | 1.50 | 1.50 | 1.50 |
| Hexyldecanol; Hexyldecyl Laurate | 3.00 | 3.00 | 3.00 | 3.00 | 3.00 | 3.00 |
| Isopropyl Palmitate | 3.00 | 3.00 | 3.00 | 3.00 | 3.00 | 3.00 |
| Dimethicone | 0.50 | 0.50 | 0.50 | 0.50 | 0.50 | 0.50 |
| Glycerin | 4.00 | 4.00 | 4.00 | 4.00 | 4.00 | 4.00 |
| Xanthan Gum | 0.49 | 0.49 | 0.49 | 0.30 | 0.49 | 0.30 |
| Fragrance | 0.5 | 0.5 | 0.5 | 0.5 | 0.5 | 0.5 |
| Tocopheryl Acetate | 0.30 | 0.30 | 0.30 | 0.30 | 0.30 | 0.30 |
| Linoleic Acid, Linolenic Acid | 0.20 | 0.20 | 0.20 | 0.20 | 0.20 | 0.20 |
| Wheat Germ Oil | 0.10 | 0.10 | — | 0.10 | 0.10 | 0.10 |
| PEG-6 Caprylic/capric glyceride | 0.10 | 0.10 | — | — | — | 0.10 |
| PEG-9 Cocoglycerides | 0.10 | 0.10 | — | — | — | 0.10 |
| Castor Oil | — | 0.10 | 0.10 | — | — | — |
| Water | QS | QS | QS | QS | QS | QS |

The compositions described in Table 1 (above) can be prepared according to conventional methods known to those skilled in the art.

Example 2

The Micro Robustness Index (MRI) of each of the compositions described in Table 1 is measured. MRI is used as a quantitative measure of a composition's ability to withstand microbial challenge. Specifically, the MRI value is the result from a challenge test assessing the efficacy of a compound/composition against a pool of microorganisms. Micropreservation is considered acceptable if the MRI value is greater than 0.75. The MRI value relates to the number of bacterial count within an induced microbiological challenge. The lower the MRI number, the greater the amount of bacteria present. Table 2 (below) describes the results of MRI evaluations performed on three exemplary compositions of the present invention (Ex. I to Ex. III) and three comparative examples (Comp. Ex. I to Comp. Ex. III).

TABLE 2

| Sample | Ex. I | Ex. II | Ex. III | Comp. Ex. I | Comp. Ex. II | Comp. Ex. III |
|---|---|---|---|---|---|---|
| MRI | 1.16 | 1.13 | 1.04 | TNTC* | 0.55 | 0.63 |

*TNTC = too numerous to count

As illustrated by the MRI data described in Table 2 (above), the compositions of the present invention comprising an inventive combination of ingredients, provide an acceptable level of micropreservation, while the comparative compositions (Comp. Ex. I to Comp. Ex. III) do not.

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

What is claimed is:

1. An aqueous personal care composition comprising:
   greater than about 60 wt. % water;
   a preservative system consisting of 0.5 wt % or greater of sodium benzoate and 0.3 wt % or greater of a $C_3$-$C_{10}$ alkyl polyol, based on the total weight of the composition; and a preservative booster consisting of a mixture of pegylated alkyl glycerides;
wherein the ratio of preservative system to preservative booster is from 3 to 1 to 6 to 1, and wherein the mixture of pegylated alkyl glycerides is PEG-9 Cocoglycerides and PEG-6 Caprylic/capric glyceride;
wherein the $C_3$-$C_{10}$ alkyl polyol is caprylyl glycol; and
wherein the composition has a pH of from 4.0 to 5.0.

2. The aqueous personal care composition according to claim 1, further comprising a hydrophobic component comprising: a wax, a silicone, an oil extract; or a combination of two or more thereof.

3. The aqueous personal care composition according to claim 1, wherein the composition is an oil-in-water emulsion.

4. The aqueous personal care composition according to claim 1, having a pH of from about 4.0 to about 4.6.

5. The aqueous personal care composition according to claim 1, wherein the composition has a viscosity greater than about 5000 cps.

6. The aqueous personal care composition according to claim 1, wherein the preservative system comprises less than about 1 wt. % of the aqueous personal care composition.

7. The aqueous personal care composition according to claim 1, wherein the ratio of preservative system to preservative booster is about 4 to 1.

8. The aqueous personal care composition according to claim 1, wherein the preservative system consists of about 0.5 wt % of sodium benzoate and about 0.3 wt % of caprylyl glycol, based on the total weight of the composition; and wherein the preservative booster consists of about 0.1 wt % of PEG-9 Cocoglycerides and about 0.1 wt % of PEG-6 Caprylic/capric glyceride, based on the total weight of the composition.

9. The aqueous personal care composition according to claim 1, wherein the preservative booster comprises about 0.1 wt % of PEG-9 Cocoglycerides and about 0.1 wt % of PEG-6 Caprylic/capric glyceride, based on the total weight of the composition.

10. The aqueous personal care composition according to claim 1, further comprising a source of ricinoleic acid.

11. The aqueous personal care composition according to claim 10, wherein the source of ricinoleic acid is castor oil.

12. The aqueous personal care composition according to claim 1, which is in a form selected from the group consisting of an ointment; a lotion; and a cream.

13. A method of improving the skin tone and/or moisturizing the skin of a mammal, comprising applying a composition according to claim 1 to the skin of a mammal in need thereof.

* * * * *